United States Patent [19]
Squicciarini et al.

[11] Patent Number: 5,728,907
[45] Date of Patent: Mar. 17, 1998

[54] TETRAALKYLMETHANES AS SYNTHETIC LUBRICANTS

[75] Inventors: Michael P. Squicciarini, Spring; William J. Heilman, Houston, both of Tex.

[73] Assignee: Pennzoil Products Company, Houston, Tex.

[21] Appl. No.: 549,485

[22] Filed: Oct. 27, 1995

[51] Int. Cl.⁶ .................................. C07C 7/20; C07C 9/00
[52] U.S. Cl. .................................................. 585/1; 585/16
[58] Field of Search ........................................ 585/7, 16, 1

[56] References Cited

U.S. PATENT DOCUMENTS

| | | |
|---|---|---|
| 3,576,898 | 4/1971 | Blake et al. . |
| 3,666,827 | 5/1972 | Carlson et al. . |
| 3,975,278 | 8/1976 | Wygant . |
| 4,755,317 | 7/1988 | Minokami et al. . |

FOREIGN PATENT DOCUMENTS

| | | | |
|---|---|---|---|
| 0 180 240 | 5/1986 | European Pat. Off. ......... | C07C 1/22 |
| 0180240 | 5/1986 | European Pat. Off. . | |

OTHER PUBLICATIONS

"Unsymmetrical Tetraalkylmethanes, IV. General Method of Synthesis of Tetraalkylmethanes", Norman Rabjohn et al., *Journal of Organic Chemistry*, vol. 21, pp. 1961–1969, Jul. 6, 1959.

Chickos, James et al. J. Chem. Thermodyn., 27(6) 693–705, 1995.

Jirovetz L. et al. Seifen, Oele, Fette, Wachse, 117(7), 252–6, 1991.

Li, Zhadin et al. Gaodeng Xuexiao Huaxue Xuebaa, 11(2), 208–11, 1990.

Cabiddu, Salvatore et al. Ann. Chim. 61(9), 634–47, 1971.

*Primary Examiner*—Alan Diamond
*Assistant Examiner*—Cephia D. Toomer
*Attorney, Agent, or Firm*—Lowe, Price, LeBlanc & Becker

[57] ABSTRACT

Tetraalkylmethanes are synthetic lubricants. The preferred structure contains four straight chain alkyl groups which may be the same or different and have from 1 to 2 or 5 to 14 carbon atoms. Mixtures are also disclosed as are novel methods for preparation of the tetraalkylmethanes.

43 Claims, No Drawings

TETRAALKYLMETHANES AS SYNTHETIC LUBRICANTS

FIELD OF THE INVENTION

This invention relates to novel tetraalkylmethanes, and mixtures thereof, their use in lubricating compositions, and novel methods for their preparation.

BACKGROUND

Tetraalkylmethanes and lubricating compositions containing them are known in the art. However, the prior art compounds and compositions including commercially available lubricants fail to achieve the substantially improved and unexpected results obtained by the present invention.

U.S. Pat. No. 3,576,898 to Blake et al. discloses hydrocarbon compounds having the structural formula:

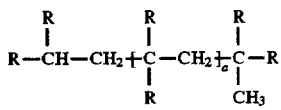

wherein each R is alkyl and a is a whole number having a value of from 0 to 1. The compounds are disclosed to be particularly useful as jet engine lubricants.

U.S. Pat. No. 3,666,827 to Carlson et al. discloses branched aliphatic hydrocarbon compounds corresponding to the following structure:

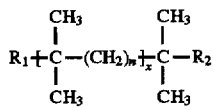

wherein $R_1$ and $R_2$ may be the same or different and are saturated, aliphatic hydrocarbons of three to 12 carbon atoms, n is four to eight and may be the same or different for repeating units, and x is one to three. Compositions containing these compounds are disclosed to be useful as lubricants and hydraulic fluids.

U.S. Pat. No. 3,975,278 to Wygant discloses tractive fluids comprising a major amount of fully saturated compounds of the general structure

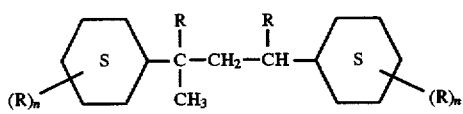

wherein each R is an alkyl of 1 to 4 carbon atoms and n is 0 to 2, and a minor amount of cyclic dimers having the general formula

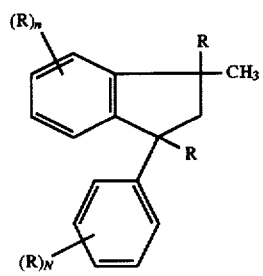

wherein each R is an alkyl of 1 to 4 carbon atoms and n is 0 to 2.

U.S. Pat. No. 4,755,317 to Minokami et al. discloses decahydronaphthalene compounds substituted with at least two substituent groups each selected from the class consisting of cyclohexyl alkyl groups and cyclohexyl groups for use in tractive drive fluids. The compounds have the following general structure

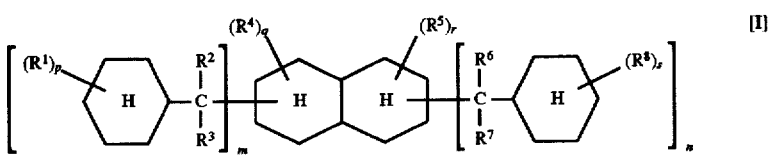

in which $R_1$, $R_2$, $R_3$, $R_4$, $R_5$, $R_6$, $R_7$, and $R_8$ each denote a hydrogen atom or an alkyl group having 1 to 4 carbon atoms, the subscripts p, q, r and s are each 1, 2, or 3 and the subscripts m and n are each zero, 1, 2 or 3 provided that m+n is equal to 2 or 3.

The Journal of Organic Chemistry, "Unsymmetrical Tetraalkyl-methanes. IV. General Method of Synthesis of Tetraalkylmethanes", Vol. 24, pp 1964–1969 (1959) discloses the synthesis of various tetraalkylmethanes.

There are many disadvantages associated with use of the above described compositions. There remains a long-felt need in the art for improved monomolecular hydrocarbon lubricants with excellent thermal stability, oxidation resistance, and low temperature flow properties. The present invention addresses this need.

SUMMARY OF THE INVENTION

It is accordingly one object of the present invention to provide novel tetraalkylmethane compounds.

A further object of the invention is to provide novel lubricating compositions which contain tetraalkylmethanes as a lubricating component.

Also provided by the present invention are lubricating compositions comprising mixtures of tetraalkylmethanes, optionally in admixture with a natural lubricant such as mineral oil or other synthetic lubricants as base oils.

Another object of the present invention is to provide lubricating compositions comprising tetraalkylmethanes and mixtures thereof, optionally in admixture with non-lubricants such as antioxidants.

Further provided by the present invention are novel methods for the preparations of the tetraalkylmethanes comprising a two or three step synthetic method.

The above and other objects of the invention will become readily apparent to those of skill in the relevant art from the following detailed description, wherein only the preferred embodiments of the invention are shown and described, simply by way of illustration of the best mode of carrying out the invention. As is readily recognized the invention is capable of modifications within the skill of the relevant art without departing from the spirit and scope of the invention.

In satisfaction of the foregoing objects and advantages of the present invention, there is provided as a broad embodiment of the invention, a class of lubricating compounds which comprise one or more tetraalkylmethanes. These lubricating tetraalkylmethanes include the individual compounds and mixtures of the tetraalkylmethane compounds. The compounds are of the following general formula:

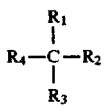

wherein $R_1$ is methyl or ethyl and $R_2$, $R_3$ and $R_4$ are the same or different and are straight chain alkyl groups having from 5 to 14 carbon atoms. In another embodiment, $R_1$, $R_2$, $R_3$ and $R_4$ are the same or different and are straight chain alkyl groups having from 5 to 14 carbon atoms. The compounds of the present invention may be symmetric or asymmetric.

In a further embodiment of the invention, there are provided novel tetraalkylmethane compositions which are useful as lubricating compositions and which are of the following general formula:

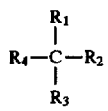

wherein $R_1$, $R_2$, $R_3$ and $R_4$ are the same or different and are straight chain alkyl groups having from 1 to 2 or 5 to 14 carbon atoms.

There are also provided by the present invention lubricating compositions which are partially synthetic lubricants and partially natural lubricants. These lubricating compositions comprise the tetraalkylmethanes, or any mixture thereof, in any proportions with a natural lubricant base such as mineral oil. Also provided are mixtures of the synthetic lubricating compositions of the present invention with other synthetic lubricants so that the resulting lubricating composition is a mixture of synthetic lubricants. Also included within the scope of the invention are mixtures of any or all of the synthetic lubricants of the present invention, alone or in admixture with other synthetic lubricants, or with natural lubricants.

The present invention further provides methods for production of the tetraalkylmethane compounds, one process comprising the steps of reacting an alkyl magnesium halide with an alkyl carbonate to produce a tertiary alcohol, reacting the tertiary alcohol with a halogen acid (i.e., an inorganic acid containing a halogen) to produce a tertiary halide, and reacting the tertiary halide with a trialkylaluminum. A second process for production of the tetraalkylmethane compounds comprises the steps of, reacting an alkylmagnesium halide with an alkyl carbonate to produce a tertiary alcohol and reacting the tertiary alcohol with titanium tetrachloride and trialkylaluminum simultaneously.

DETAILED DESCRIPTION OF INVENTION

The present invention is broadly concerned with lubricating compositions which comprise certain tetraalkylmethanes, or mixtures thereof, and methods of preparation. The invention is also concerned with a class of novel tetraalkylmethane compounds, and methods for their preparation.

In a main embodiment of the invention, novel synthetic fluids which are lubricating compositions comprise a group of tetraalkylmethanes of the following formula:

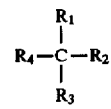

wherein $R_1$, $R_2$, $R_3$ and $R_4$ are the same or different and are straight chain alkyl groups having 1 to 2 or 5 to 14 carbon atoms.

These tetraalkylmethanes have been found to provide excellent lubricating characteristics which make them useful as lubricants in internal combustion engines and in other areas where good lubricity is required. The lubricants may comprise individual tetraalkylmethanes or mixtures thereof. The compounds provide the appropriate specific gravity, refractive indices, viscosities, and low and high temperature characteristics which are required for an outstanding lubricant. Table 1 shows the rheological properties of various tetraalkylmethanes.

Preferred groups of tetraalkylmethane lubricants are those wherein $R_1$ is methyl or ethyl. Also preferred are those compounds wherein $R_2$, $R_3$ and $R_4$ are n-pentyl, n-hexyl, n-heptyl, n-octyl, n-nonyl, n-decyl, n-undecyl, n-dodecyl, n-tridecyl or n-tetradecyl; $R_2$, $R_3$ and $R_4$ are n-pentyl, n-hexyl or n-heptyl; $R_2$, $R_3$ and $R_4$ are n-octyl, n-nonyl or n-decyl; $R_2$, $R_3$ and $R_4$ are n-octyl; $R_2$, $R_3$ and $R_4$ are n-nonyl; $R_2$, $R_3$ and $R_4$ are n-decyl; $R_2$, $R_3$ and $R_4$ are n-dodecyl, n-tridecyl or n-tetradecyl.

Other preferred embodiments include those compounds wherein $R_2$ is n-pentyl, n-hexyl, n-heptyl, or n-octyl and $R_3$ and $R_4$ are n-nonyl, n-decyl, n-undecyl, n-dodecyl, n-tridecyl or n-tetradecyl; $R_2$ and $R_3$ are n-pentyl, n-hexyl, n-heptyl, n-octyl and $R_4$ is n-nonyl, n-decyl, n-undecyl, n-dodecyl, n-tridecyl or n-tetradecyl;

$R_1$, $R_2$, $R_3$ and $R_4$ are n-pentyl, n-hexyl, n-heptyl, n-octyl, n-nonyl, n-decyl, n-undecyl, n-dodecyl, n-tridecyl or n-tetradecyl; $R_1$, $R_2$, $R_3$ and $R_4$ are n-pentyl, n-hexyl or n-heptyl; $R_1$, $R_2$, $R_3$ and $R_4$ are n-octyl, n-nonyl or n-decyl; $R_1$, $R_2$, $R_3$ and $R_4$ are n-hexyl; $R_1$, $R_2$, $R_3$ and $R_4$ are n-heptyl; $R_1$, $R_2$, $R_3$ and $R_4$ are n-octyl; $R_1$, $R_2$, $R_3$ and $R_4$ are n-nonyl; $R_1$ and $R_2$ are n-pentyl, n-hexyl and n-heptyl and $R_3$ and $R_4$ are n-octyl, n-nonyl, n-decyl, n-undecyl, n-dodecyl, n-tridecyl or n-tetradecyl;

In further preferred embodiments, the tetraalkylmethane lubricants have varying ranges of carbon atoms such as 17 to 23 carbon atoms, 24 to 30 carbon atoms, 31 to 37 carbon atoms, 38 to 44 carbon atoms, or 45 to 57 carbon atoms.

There is also provided by the present invention partial synthetic lubricant compositions in which the tetraalkylmethanes, used either alone or in admixture, are mixed with a natural base fluid such as mineral oil to form a lubricant. Compositions of this type may contain about 10 to 90% of any of the synthetic lubricants of this invention mixed with 90 to 10% of a mineral oil base fluid. Compositions of this type show enhanced lubricant properties.

In a further embodiment of the invention, mixtures of the tetraalkylmethanes, used either alone or in admixture, may be mixed with other synthetic lubricants such as poly-alpha-olefin, esters and polyol esters. These mixtures may include 10 to 90% of the synthetic tetraalkylmethanes, mixed with 90 to 10% of any other compatible synthetic lubricant.

In an additional embodiment of the invention, mixtures of the tetraalkylmethanes may be mixed with one or more non-lubricant additives. These compositions comprise the tetraalkylmethanes, or any mixture thereof, in any proportions with a non-lubricating additive. Examples of non-lubricant additives include oxidation inhibitors, rust inhibitors, antiwear agents, detergents-dispersants, pour point depressants, viscosity-index (VI) improvers and foam inhibitors.

Various organic compounds may be added to the lubricating compositions of the present invention to retard the oxidation process. Suitable oxidation inhibitors include phenols or arylamines.

Rust inhibitors are surface active materials that are preferentially adsorbed as a film on metal surfaces to protect then from attach by moisture. Suitable rust inhibitors include metal dithiocarbamates, alkenyl succinic acids and their derivates and propoxylated or ethoxylated alkyl phenols.

Antiwear agents may be added to the compositions of the present invention to produce a surface film, by either a chemical or physical adsorption mechanism to minimize friction and wear under boundary-lubrication conditions. Suitable antiwear agents include oxygen containing compounds, sulfur containing compounds, compounds containing both oxygen and sulfur, organic chlorine compounds, organic sulfur compounds such as sulfurized fats or olefins, compounds containing both chlorine and sulfur, organic phosphorous compounds, and organic lead compounds. Preferred antiwear agents include zinc dialkyldithiophosphates.

Detergents-dispersants may be a component of the present lubricating compositions to adsorb on insoluble particles, thereby maintaining them as a suspension in the oil to minimize deposits and to maintain cleanliness of, for example, rings valves, and cylinder walls. Suitable detergents-dispersants include phenates, sulfonates, non-ionic dispersants such as alkyl succinimides or Mannich bases of phenols.

Suitable pour point depressants include polyacrylate and methacrylate.

Suitable viscosity-index (VI) improvers include olefin copolymer or polyacrylate.

Foam inhibitors may be useful for defoaming the lubricating compositions when used in internal combustion engines, turbines, gear sets, and aircraft applications. Suitable foam inhibitors include dimethylsiloxanes and polyethers.

In a further embodiment of the invention, there are also provided a novel group of tetraalkylmethanes, which have been designed to contain a single central quaternary carbon atom and to eliminate tertiaryhydrogen atoms, are of the following formula:

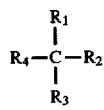

wherein $R_1$ is methyl or ethyl and $R_2$, $R_3$ and $R_4$ are the same or different and are straight chain alkyl groups having from 5 to 14 carbon atoms. Straight chain alkyl groups having from 5 to 14 carbon atoms include n-pentyl, n-hexyl, n-heptyl, n-octyl, n-nonyl, n-decyl, n-undecyl, n-dodecyl, n-tridecyl and n-tetradecyl.

A group of preferred compounds are those wherein $R_2$, $R_3$ and $R_4$ are n-pentyl, n-hexyl or n-heptyl; $R_2$, $R_3$ and $R_4$ are n-octyl, n-nonyl or n-decyl; $R_2$, $R_3$ and $R_4$ are n-octyl; $R_2$, $R_3$ and $R_4$ are n-nonyl; $R_2$, $R_3$ and $R_4$ are n-decyl; $R_2$, $R_3$ and $R_4$ are n-undecyl, n-dodecyl, n-tridecyl or n-tetradecyl; $R_2$ is n-pentyl, n-hexyl, n-heptyl, n-octyl and $R_3$ and $R_4$ are n-nonyl, n-decyl, n-undecyl, n-dodecyl, n-tridecyl or n-tetradecyl; $R_2$ and $R_3$ are n-pentyl, n-hexyl, n-heptyl, n-octyl and $R_4$ is n-nonyl, n-decyl, n-undecyl, n-dodecyl, n-tridecyl or n-tetradecyl.

In further preferred embodiments, the tetraalkylmethane compounds have varying ranges of carbon atoms such as 17 to 23 carbon atoms, 24 to 30 carbon atoms, 31 to 37 carbon atoms, or 38 to 44 carbon atoms.

In an additional embodiment of the invention, there are also provided a novel group of tetraalkylmethanes, which have been designed to contain a single central quaternary carbon atom and to eliminate tertiary hydrogen atoms, are of the following formula:

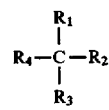

wherein $R_1$, $R_2$, $R_3$ and $R_4$ are the same or different and are straight chain alkyl groups having from 5 to 14 carbon atoms. Straight chain alkyl groups having from 5 to 14 carbon atoms are n-pentyl, n-hexyl, n-heptyl, n-octyl, n-nonyl, n-decyl, n-undecyl, n-dodecyl, n-tridecyl and n-tetradecyl.

A group of preferred compounds are those wherein $R_1$, $R_2$, $R_3$ and R4 are n-pentyl, n-hexyl or n-heptyl; $R_1$, $R_2$, $R_3$ and $R_4$ are n-octyl, n-nonyl or n-decyl; $R_1$, $R_2$, $R_3$ and $R_4$ are n-hexyl; $R_1$, $R_2$, $R_3$ and $R_4$ are n-heptyl; $R_1$, $R_2$, $R_3$ and $R_4$ are n-octyl; $R_1$, $R_2$, $R_3$ and $R_4$ are n-nonyl; $R_1$ and $R_2$ are n-pentyl, n-hexyl or n-heptyl and $R_3$ and $R_4$ are n-octyl, n-nonyl, n-decyl, n-undecyl, n-dodecyl, n-tridecyl or n-tetradecyl.

In further preferred embodiments, the tetraalkylmethane compounds have varying ranges of carbon atoms such 25 to 30 carbon atoms, 31 to 35 carbon atoms, 36 to 45 carbon atoms, and 46 to 57 carbon atoms.

Particularly preferred compounds which are also useful as lubricants include the following:

8-methyl-8-heptyldecane
8-methyl-8-heptylhexadecane
9-methyl-9-heptylheptadecane
9-methyl-9-octylheptadecane
10-methyl-10-nonylnonadecane
10-methyl-10-octylnonadecane
9-methyl-9-octyloctadecane
11-methyl-11-decylhenicosane
11-methyl-11-nonylhenicosane
10-methyl-10-nonylicosane
12-methyl-12-decyltricosane
11-methyl-11-decyl docosane
12-methyl-12-undecyltricosane
8,8-diheptylpentadecane
8,8-diheptylhexadecane
9,9-diheptylheptadecane
9-heptyl-9-octylheptadecane
9,9-dioctylheptadecane
9,9-dioctyloctadecane
10,10-dioctylnonadecane
10-octyl-10-nonylnonadecane
10,10-dinonylnonadecane.

The tetraalkylmethanes are prepared by a process comprising the steps of reacting an n-alkyl magnesium halide with an alkyl carbonate to produce a tertiary alcohol, reacting the tertiary alcohol with a halogen acid (i.e., an inorganic acid containing a halogen) to produce a tertiary halide, and reacting the tertiary halide with a tri-n-alkylaluminum. A preferred dialkyl carbonate is diethyl carbonate. A preferred halogen acid is hydrochloric acid. A preferred trialkylaluminum is trimethylaluminum. Also, the Grignard reagent is prepared by reacting metallic magnesium with an n-alkyl halide.

In a further separate and preferred embodiment for preparing the tetraalkylmethanes of the present invention, the tetraalkylmethanes are prepared by a process comprising the steps of reacting an n-alkylmagnesium halide with an alkyl carbonate to produce a tertiary alcohol, and reacting the tertiary alcohol with titanium tetrachloride and trialkylaluminum. The Grignard reagent is prepared by reacting metallic magnesium with an n-alkyl halide.

A preferred trialkylaluminum is trimethylaluminum and a preferred dialkyl carbonate is diethyl carbonate.

The following examples are merely illustrative of the present invention and they should not be considered as limiting the scope of the invention in any way, as these examples and other equivalents will become more apparent to those skilled in the art in light of the present disclosure.

EXAMPLE 1

Preparation of 9-Methyl-9-Octylheptadecane (Compound A)

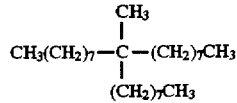

This compound may be prepared in the following manner. Three moles of 1-bromooctane are slowly added to 3 moles of magnesium turnings in 0.6 liters of anhydrous ethyl ether (nitrogen atmosphere). One mole of diethyl carbonate in 0.151 anhydrous ethyl ether is slowly added to the mixture. The mixture is stirred for one hour at 30° C., then the mixture is slowly poured into 1.8 liters of a cold 10% HCl solution. The organic layer is dried with magnesium sulfate and the ethyl ether is evaporated off to give tri-n-octylcarbinol. One mole of tri-n-octylcarbinol is added to a mixture of 0.2 liters of methylene chloride and 0.32 moles calcium chloride. Approximately 1.5 moles of HCl gas is slowly bubbled through the solution. The product mixture is then washed with 1 liter of a 10% sodium carbonate solution. The organic layer is dried with magnesium sulfate and the methylene chloride is evaporated off. One mole of tri-n-octylmethylchloride is added to 0.75 liters of methylene chloride and the solution is blanketed with nitrogen and is cooled to 0° C. 0.33 moles of trimethylaluminum is then added and the mixture is allowed to warm to room temperature. The mixture is slowly quenched with 50 ml of water followed by washing with 1 liter of a 10% HCl solution. The organic layer is dried with magnesium sulfate and the solvent is evaporated to give tri-n-octylmethylmethane.

EXAMPLE 2

Preparation of 11-Methyl-11-Decylhenicosane (Compound B)

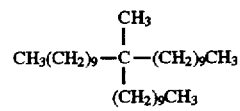

Three moles of 1-bromodecane was slowly added to 3 moles of magnesium turnings in 0.6 liters of anhydrous ethyl ether (nitrogen atmosphere). One mole of diethyl carbonate in 0.151 anhydrous ethyl ether was slowly added to the mixture. After stirring for one hour at 30° C., the mixture was slowly poured into 1.8 liters of a cold 10% HCl solution. The organic layer was dried with magnesium sulfate and the ethyl ether evaporated off to give tri-n-decylcarbinol.

One mole of tri-n-decylcarbinol was added to a mixture of 0.2 liters of methylene chloride and 0.32 moles calcium chloride. Approximately 1.5 moles of HCl gas was slowly bubbled through the solution. The product mixture is then washed with 1 liter of a 10% sodium carbonate solution. The organic layer is dried with magnesium sulfate and the methylene chloride evaporated off to give a 90% yield of tri-n-decylmethylchloride.

One mole of tri-n-decylmethylchloride was added to 0.75 liters of methylene chloride and the solution was blanketed with nitrogen and cooled to 0° C. 0.33 moles of trimethylaluminum was then added and the mixture was allowed to warm to room temperature. The mixture was slowly quenched with 50 ml of water followed by washing with 1 liter of a 10% HCl solution. The organic layer was dried with magnesium sulfate and the solvent was evaporated to give tri-n-decylmethylmethane after vacuum distillation at 225 C/0.5 torr. The yield was 75%.

Alternatively, the 0.1 moles of the synthesized tri-n-decylcarbinol was added to 0.2 liters of methylene chloride. The mixture was covered with a blanket of nitrogen and cooled to 0° C. 0.050 mole titanium tetrachloride was added to the mixture and the solution was stirred 2–3 hours at 0° C. 0.066 mole trimethylaluminum was added and the mixture was allowed to warm to room temperature. The reaction was quenched with water and washed with 0.1 liter of a 20% HCl solution. The organic layer was dried with magnesium sulfate and the methylene chloride removed to give a yield of 70% tri-n-decylmethylmethane.

EXAMPLE 3

Preparation of 9,9-Dioctylheptadecane (Compound C)

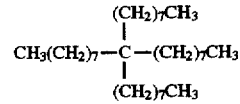

This compound may be prepared in the following manner. Three moles of n-octylbromide are slowly added to 3 moles of magnesium turnings in 0.6 liters of anhydrous ethyl ether (nitrogen atmosphere). One mole of diethyl carbonate in 0.151 anhydrous ethyl ether is slowly added to the mixture. The mixture is stirred for one hour at 30° C., then the mixture is slowly poured into 1.8 liters of a cold 10% HCl solution. The organic layer is dried with magnesium sulfate and the ethyl ether is evaporated off to give tri-n-octylcarbinol.

One mole of tri-n-octylcarbinol is added to a mixture of 0.2 liters of methylene chloride and 0.32 moles calcium chloride. Approximately 1.5 moles of HCl gas is slowly bubbled through the solution. The product mixture is then washed with 1 liter of a 10% sodium carbonate solution. The organic layer is be dried with magnesium sulfate and the methylene chloride is evaporated off.

One mole of tri-n-octylmethylchloride is added to 0.75 liters of methylene chloride and the solution is blanketed with nitrogen and is cooled to 0° C. 0.33 moles of tri-n-octylaluminum is then added and the mixture is allowed to warm to room temperature. The mixture is slowly quenched with 50 ml of water followed by washing with 1 liter of a 10% HCl solution. The organic layer is dried with magnesium sulfate and the solvent is evaporated to give tetra-n-octylmethane.

EXAMPLE 4

Preparation of 10,10-Didecylhenicosane
(Compound D)

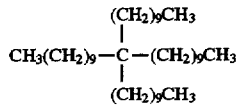

This compound may be prepared in the following manner. 0.1 mole of tri-n-decylcarbinol is added to 0.2 liters of methylene chloride. The mixture is covered with a blanket of nitrogen and cooled to 0° C. 0.050 mole titanium tetrachloride is added to the mixture and the solution is stirred 2–3 hours at 0° C. 0.066 mole tri-n-decylaluminum is added and the mixture is allowed to warm to room temperature. The reaction is quenched with water and is washed with 0.1 liter of a 20% HCl solution. The organic layer is dried with magnesium sulfate and the methylene chloride is removed to give tetra-n-decylmethane.

EXAMPLE 5

Preparation of 11-Octyl-11-Decylpentacosane
(Compound E)

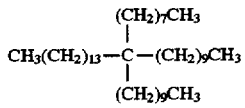

Decylmagnesium bromide (0.66 mole) in ethyl ether is slowly added to 0.33 moles of diethylcarbonate in 100 ml ethyl ether and stirred for one hour at 30° C. (nitrogen atmosphere). Tetradecylmagnesium bromide (0.33 moles) is slowly added to the solution and stirred for one hour at 30° C. The mixture is then slowly poured into 600 ml of a cold 10% HCl solution. The organic layer is dried with magnesium sulfate and the ethyl ether evaporated off to give di-n-decyl-n-tetradecylcarbinol.

One mole of di-n-decyl-n-tetradecylcarbinol is added to 0.2 liters of methylene chloride and 0.32 moles calcium chloride. Approximately 1.5 moles of HCl gas is slowly bubbled through the solution. The product mixture is then washed with 1 liter of a 10% sodium carbonate solution. The organic layer is dried with magnesium sulfate and the methylene chloride is evaporated off to give di-n-decyl-n-tetradecyl-methylchloride.

One mole of di-n-decyl-n-tetradecylmethylchloride is added to 0.75 liters of methylene chloride and the solution is blanketed with nitrogen and cooled to 0° C. Tri-n-octylaluminum, 0.33 moles, is then added and the mixture was allowed to warm to room temperature. The mixture is slowly quenched with 50 ml of water followed by washing with 1 liter of a 10% HCl solution. The organic layer was dried with magnesium sulfate and the solvent evaporated to give di-n-decyl-n-tetradecyl-n-octylmethane.

EXAMPLE 6

Preparation of 15-Octyl-15-Nonyltetratriacontrane
(Compound F)

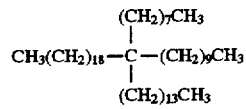

n-Nonadecylmagnesium bromide (0.33 moles) in ethyl ether is slowly added to 0.33 mole of diethylcarbonate in 100 ml diethyl ether and stirred for one hour at 30° C. (nitrogen atmosphere). n-Tetradecylmagnesium bromide (0.33 mole) is slowly added to the solution and stirred for one hour at 30° C. n-Decylmagnesium bromide (0.33 mole) is slowly added to the solution and stirred for one hour at 30° C. The mixture is then slowly poured into 600 ml of a cold 10% HCl solution. The organic layer is dried with magnasium sulfate and the ethyl ether evaporated off to give n-nonadecyl-n-tetradecyl-n-decylcarbinol.

One mole of n-nonadecyl-n-tetradecyl-n-decylcarbinol is added to 0.2 liters of methylene chloride and 0.32 moles calcium chloride. Approximately 1.5 moles of HCl gas is slowly bubbled through the solution. The product mixture is then washed with 1 liter of a 10% sodium carbonate solution. The organic layer is dried with magnesium sulfate and the methylene chloride is evaporated off to give n-nonadecyl-n-tetradecyl-n-decylmethylchloride.

One mole of n-nonadecyl-n-tetradecyl-n-decylmethylchloride is added to 0.75 liters of methylene chloride and the solution is blanketed with nitrogen and cooled to 0° C. Tri-n-octylaluminum, 0.33 moles, is then added and the mixture is allowed to warm to room temperature. The mixture is slowly quenched with 50 ml of water followed by washing with 1 liter of a 10% HCl solution. The organic layer was dried with magnesium sulfate and the solvent evaporated to give n-nonadecyl-n-tetradecyl-n-decyl-n-octylmethane.

EXAMPLE 7

To evaluate the tetraalkylmethanes for lubricating properties, tests which are relevant to evaluate the properties of lubricants and functional fluids were carried out. Set forth in Table 1 are the pour point (ASTM D97), kinematic viscosity (viscosity at 40° C. and 100° C.) and viscosity index (ASTM D2270) of the tetraalkylmethanes prepared in Examples 1–6 (compounds A–F).

TABLE 1

Rheological Properties of Tetraalkylmethanes

| | Pour Point (°C.) | KINEMATIC VISCOSITY (mm²/sec) | | Viscosity Index |
|---|---|---|---|---|
| | | 40° C. | 100° C. | |
| A | <-50 | 11.09 | 2.84 | 101 |
| tri(n-octyl)methylsilane | <-50 | 7.41 | 2.33 | 138 |
| B | <-54 | 19.64 | 4.32 | 130 |
| 4 cSt PAO | -70 | 16.8 | 3.9 | 129 |
| 6 cSt PAO | -68 | 31.0 | 5.9 | 138 |
| C | <-50 | 23.5 | 4.72 | 121 |
| D | 2 | 32.5 | 6.29 | 164 |
| E | -12 | 39.45 | 7.25 | 150 |
| F | solid at RT | | | |

A = Tri-n-octylmethylmethane,
B = Tri-n-decylmethylmethane,
C = Tetra-n-octylmethane,
D = Tetra-n-decylmethane,
E = di-n-decyl-n-octyl-n-tetradecylmethane,
F = n-octyl-n-decyl-n-tetradecyl-n-nonadecylmethane.

Pour point, the temperature at which fluid solidification occurs, is a measure of low temperature stability. Compounds A, B and C had favorable low-temperature flow as exhibited by pour points below −50° C. Pour point increased with increasing carbon chain length. The pour point of the higher molecular weight tetra(n-decyl)methane, compound D, was at least 52° C. greater than the symmetrically structured tetra(n-octyl)methane, compound C. For the tri(n-alkyl)methylmethanes (compounds A and B), increasing the alkyl chain length did not appear to raise the pour point. Relative to symmetrically structured compound D, the higher molecular weight but unsymmetrical compound E shows a decrease in pour point of 14° C. The pour points of compound A and silahydrocarbon tri(n-octyl)methylsilane were both below −50° C.

Comparing the symmetrically structured tetra(n-octyl) methane, compound C, to higher molecular weight tetra(n-decyl)methane, compound D, it is apparent that the viscosity at 40° C. and 100° C. increased 9 mm²/sec (cSt) and 1.6 mm²/sec(cSt) respectively. For the tri(n-alkyl methyl-methanes (compounds A and B) increasing the alkyl chain length increased the kinematic viscosity. The viscometrics for compound B have been found to be comparable to 4 mm²/sec(cSt) PAO.

The viscosity index is a measure of the extent of viscosity change with change in temperature. The higher the viscosity index, the less the viscosity of the fluid changes with temperature. Oils with a viscosity index of 130 or above and pour points less than −50° C. are desirable for the formulation of lower viscosity grade motor oils such as 5W-30. Comparing the symmetrically structured tetra(n-octyl) methane, compound C, to higher molecular weight tetra(n-decyl)methane, compound D, it can be seen that the viscosity index increased by 43. For the tri(n-alkyl) methylmethanes (compounds A and B) increasing the alkyl chain length increased the viscosity index by 29. Relative to symmetrically structured D, the higher molecular weight but unsymmetrical Structure E shows an increase in viscosity. The viscosity index of compound A was lower than that of silahydrocarbon tri(n-octyl)methylsilane.

EXAMPLE 8

The tetraalkylmethanes were further evaluated for oxidative stability with pressure differential scanning calorimetry (PDSC). PDSC determines the induction time for enthalpy change (oxidation) at an elevated temperature under an atmosphere of pressurized oxygen. The instrument used for this evaluation was a Mettler PDSC 27 HP. Samples of 2 mg were weighed into an aluminum pan and the pressure cell purged for 5 minutes with oxygen. The analysis was carried out at two temperatures, 175° C. and 165° C., at a ramp rate of 50° C./minute to temperature. At temperature, the cell pressure was maintained at 3.4 MPa (500 psi). At either temperature the induction time repeatability was less than two minutes. The results of this evaluation are set forth in Table 2.

TABLE 2

PDSC Induction Time for Onset of Oxidation

| | Induction Time (Min) | |
|---|---|---|
| | 175° C. | 165° C. |
| A | 18.3 | 41.9 |
| Tri(n-octyl)methylsilane | 19.4 | 46.4 |
| B | 21.7 | 51.9 |
| 4 cSt PAO | 11.05 | 24.0 |
| 6 cSt PAO | 10.4 | 23.9 |
| C | 18.0 | 46.4 |
| D | 20.3 | 47.3 |
| E | 21.1 | 48.6 |

The tetraalkylmethanes show substantially greater induction times relative to PAO indicating a better thermooxidative stability for the tetraalkylmethanes of the present invention. While not wishing to be bound by any particular theory, the present inventors are of the opinion that the better stability of the tetraalkylmethanes may be explained by the fact that the tetraalkylmethanes of the present invention do not contain any tertiary hydrogen, unlike the branched decene oligomer of a PAO. The rate of oxidation of a hydrocarbon is largely dependent by the ease of hydrogen abstraction in the propagation sequence of oxidation. The greater stability of a tertiary radical as compared with a primary or secondary radical would lead to a faster rate of attack by alkyl peroxide radicals for PAO and subsequently a faster rate of oxidative degradation. The tetraalkyl-methanes of the present invention could be more resistive to oxidation relative to PAO because only higher energy primary and secondary radicals can be formed. The silahydrocarbon tested here has an induction time similar to the analogous structured tetraalkylmethanes. The lack of tertiary hydrogen in tri(n-ocyl)methylsilane most likely enhances oxidative stability relative to PAO. Of the tested tetraalkylmethanes, compound B demonstrates the best oxidative stability followed by the higher molecular weight hydrocarbons E and F. The methyl group on compound B does not appear detrimental to oxidative stability.

EXAMPLE 9

The oxidative stability of the tetra(n-alkyl)methanes of the present invention was further evaluated with a rotary bomb ASTM D 2112 method. The fluids tested were formulated with 0.035 wt. %, 2,6-di-tertbutylphenol. 50 ml of the formulated oil and 5 ml water were added into a sample container containing a copper coil. The bomb was heated for 140° C. under 0.6 MPa (90 psi) of oxygen. The induction time was recorded for 0.2 MPa (25 psi) decrease in oxygen. The results of this evaluation are shown in Table 3.

TABLE 3

Rotary Bomb Oxidation Test

| Antioxidant Conc. 0.035% | Oxidation Induction Time (Min) |
|---|---|
| B | 1254 |
| 4cStPAO | 521 |
| C | 1214 |
| D | 1047 |

As in PDSC, the tetraalkylmethanes show good oxidative stability with induction times at least twice as long as 4 mm$^2$/sec(cSt) PAO.

EXAMPLE 10

To evaluate the tetraalkylmethanes of the present invention for fluid volatility and thermal stability, thermal gravimetric analysis was performed under nitrogen. A Dupont 951 thermogravimetric analyzer was used. The fluids were run at heating rates of 20° C. per minute.

TABLE 4

Thermal Gravimetric Analysis

| Temperature (°C.) at Weight % Loss of | 5% | 50% | 95% |
|---|---|---|---|
| A | 209 | 286 | 305 |
| tri(n-octyl)methylsilane | 219 | 283 | 300 |
| B | 272 | 317 | 334 |
| 4 cSt PAO | 251 | 306 | 325 |
| 6 cSt PAO | 262 | 316 | 357 |
| C | 276 | 329 | 346 |
| D | 298 | 364 | 383 |
| E | 300 | 360 | 382 |

The temperature at percent off for compounds C and B are similar to 4 and 6 mm$^2$/sec (cSt) PAO. This might be due to similar molecular weight ranges. The 4 mm$^2$/sec (cSt) PAO consists primarily of 1-decene trimer (molecular weight of 422), with small amounts of decene tetramer and pentamer present. No apparent difference in temperatures was apparent between compound A and tri(n-octyl)methylsilane (molecular weight of 382). This may indicate that a silicon central atom does not substantially decrease volatility.

In contrast to the effect that the branched structure of PAO has on thermal stability and volatility, the greater steric straining and star structure of the tetraalkylmethanes of the present invention do not appear to be detrimental to thermal stability or volatility.

EXAMPLE 11

The lubricity characteristics of the tetraalkylmethanes compounds of the present invention were evaluated using the four-ball wear test, ASTM D4172. The fluids were tested neat to examine inherent lubricity and the results are shown in Table 5.

TABLE 5

Four Ball Wear Data

| | Average Wear Scar (mm) |
|---|---|
| A | 0.89 |
| tri(n-octyl)methylsilane | 0.99 |
| B | 0.86 |
| 4 cSt PAO | 0.78 |
| 6 cSt PAO | 0.81 |
| C | 0.86 |
| D | 0.81 |
| E | 0.71 |

The higher molecular weight compounds (i.e., compounds E and D) had an average wear scar less than or equivalent to PAO. Compounds A, B and C had somewhat greater average wear scars than PAO, e.g., 0.86 mm for compound B as compared with 0.78 mm for 4 mm$^2$/sec PAO. The silahydrocarbon was found to have a significantly higher average wear scar of 0.99 mm.

EXAMPLE 12

Engine oil was made with tri-n-decylmethylmethane, 5W-30 motor oil.

| Formulation | % by weight |
|---|---|
| Tri-n-decylmethylmethane | 32.4 |
| PAO 8 cSt | 40.2 |
| Emkarate 1550 | 10.9 |
| Shell Vis 200 | 6.3 |
| Rohm & Haas Acryloid 3004 | 0.1 |
| Chevron Oloa 9201 | 10.1 |
| Properties | |
| Viscosity, 100° C. | 11.16 cSt |
| Viscosity, 40° C. | 64.39 cSt |
| Viscosity index | 167 |
| Pour Point | <–57° C. |

EXAMPLE 13

Thermal Analysis of 5W-30 Synthetic Motor Oils

| | TGA (Temperature (°C.) at percent off) | | | PDSC (Time, Min.) |
|---|---|---|---|---|
| | 5% | 50% | 95% | |
| Commercial synthetic | 268 | 352 | 418 | 22.0 |
| Tri-n-decylmethylmethane formulated 5W-30 | 275 | 353 | 437 | 24.5 |

EXAMPLE 14

Four Ball Wear Data

|  | Average Wear Scar (mm) |
|---|---|
| Commercial 5W-30 | 0.45 |
| Tri-n-decylmethylmethane formulated 5W-30 | 0.43 |
| Four ball wear conditions: (ASTM D4172) | 75° C., 1200 rpm, 60 min; 392N |

The purpose of the above description and examples is to illustrate some embodiments of the present invention without implying any limitation. It will be apparent to those of skill in the art that various modifications and variations may be made to the present invention without departing from the spirit or scope of the invention.

We claim:

1. A compound of the formula:

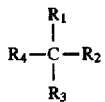

wherein $R_1$, $R_2$, $R_3$ and $R_4$ are the same or different and are straight chain alkyl groups having from 5 to 14 carbon atoms with the proviso that 8,8-dipentyl heptadecane, 7,7-dihexyltridecane, 8-pentyl-8-hexylhexadecane, and 6,6-dipentylundecane are excluded.

2. A compound according to claim 1, wherein $R_1$, $R_2$, $R_3$ and $R_4$ are selected from the group consisting of n-pentyl, n-hexyl, n-heptyl, n-octyl, n-nonyl, n-decyl, n-undecyl, n-dodecyl, n-tridecyl and n-tetradecyl.

3. A compound according to claim 1, wherein $R_1$, $R_2$, $R_3$ and $R_4$ are selected from the group consisting of n-pentyl, n-hexyl and n-heptyl.

4. A compound according to claim 1, wherein $R_1$, $R_2$, $R_3$ and $R_4$ are selected from the group consisting of n-octyl, n-nonyl and n-decyl.

5. A compound according to claim 3, wherein $R_1$, $R_2$, $R_3$ and $R_4$ are n-hexyl.

6. A compound according to claim 3, wherein $R_1$, $R_2$, $R_3$ and $R_4$ are n-heptyl.

7. A compound according to claim 4, wherein $R_1$, $R_2$, $R_3$ and $R_4$ are n-octyl.

8. A compound according to claim 4, wherein $R_1$, $R_2$, $R_3$ and $R_4$ are n-nonyl.

9. A compound according to claim 1, wherein $R_1$ and $R_2$ are selected from the group consisting of n-pentyl, n-hexyl and n-heptyl and $R_3$ and $R_4$ are selected from the group consisting of n-octyl, n-nonyl, n-decyl, n-undecyl, n-dodecyl, n-tridecyl and n-tetradecyl.

10. A compound according to claim 1 having 25 to 30 carbon atoms.

11. A compound according to claim 1 having 31 to 35 carbon atoms.

12. A compound according to claim 1 having 36 to 45 carbon atoms.

13. A compound according to claim 1 having 46 to 57 carbon atoms.

14. A mixture of at least two compounds as defined in claim 1, wherein each of $R_1$, $R_2$, $R_3$ and $R_4$ is individually and independently selected from alkyl groups of varying carbon chain lengths.

15. A lubricating composition comprising at least one compound of the formula:

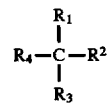

wherein $R_1$, $R_2$, $R_3$ and $R_4$ are the same or different and are straight chain alkyl groups having 1 to 2 or 5 to 14 carbon atoms and an additive acceptable for use in said lubricating composition.

16. A lubricating composition according to claim 15, wherein $R_1$ is methyl or ethyl and $R_2$, $R_3$ and $R_4$ are selected from the group consisting of n-pentyl, n-hexyl, n-heptyl, n-octyl, n-nonyl, n-decyl, n-undecyl, n-dodecyl, n-tridecyl and n-tetradecyl.

17. A lubricating composition according to claim 16, wherein $R_2$, $R_3$ and $R_4$ are selected from the group consisting of n-pentyl, n-hexyl and n-heptyl.

18. A lubricating composition according to claim 16, wherein $R_2$, $R_3$ and $R_4$ are selected from the group consisting of n-octyl, n-nonyl and n-decyl.

19. A lubricating composition according to claim 18, wherein $R_2$, $R_3$ and $R_4$ are n-octyl.

20. A lubricating composition according to claim 18, wherein $R_2$, $R_3$ and $R_4$ are n-nonyl.

21. A lubricating composition according to claim 18, wherein $R_2$, $R_3$ and $R_4$ are n-decyl.

22. A lubricating composition according to claim 16, wherein $R_2$, $R_3$ and $R_4$ are selected from the group consisting of n-undecyl, n-dodecyl, n-tridecyl and n-tetradecyl.

23. A lubricating composition according to claim 16, wherein $R_2$ is selected from the group consisting of n-pentyl, n-hexyl, n-heptyl, n-octyl and $R_3$ and $R_4$ are selected from the group consisting of n-nonyl, n-decyl, n-undecyl, n-dodecyl, n-tridecyl and n-tetradecyl.

24. A lubricating composition according to claim 16, wherein $R_2$ and $R_3$ are selected from the group consisting of n-pentyl, n-hexyl, n-heptyl, n-octyl and $R_4$ is selected from the group consisting of n-nonyl, n-decyl, n-undecyl, n-dodecyl, n-tridecyl and n-tetradecyl.

25. A lubricating composition according to claim 15, wherein $R_1$, $R_2$, $R_3$ and $R_4$ are selected from the group consisting of n-pentyl, n-hexyl, n-heptyl, n-octyl, n-nonyl, n-decyl, n-undecyl, n-dodecyl, n-tridecyl and n-tetradecyl.

26. A lubricating composition according to claim 15, wherein $R_1$, $R_2$, $R_3$ and $R_4$ are selected from the group consisting of n-pentyl, n-hexyl and n-heptyl.

27. A lubricating composition according to claim 15, wherein $R_1$, $R_2$, $R_3$ and $R_4$ are selected from the group consisting of n-octyl, n-nonyl and n-decyl.

28. A lubricating composition according to claim 26, wherein $R_1$, $R_2$, $R_3$ and $R_4$ are n-hexyl.

29. A lubricating composition according to claim 26, wherein $R_1$, $R_2$, $R_3$ and $R_4$ are n-heptyl.

30. A lubricating composition according to claim 27, wherein $R_1$, $R_2$, $R_3$ and $R_4$ are n-octyl.

31. A lubricating composition according to claim 27, wherein $R_1$, $R_2$, $R_3$ and $R_4$ are n-nonyl.

32. A lubricating composition according to claim 15, wherein $R_1$ and $R_2$ are selected from the group consisting of n-pentyl, n-hexyl and n-heptyl and $R_3$ and $R_4$ are selected from the group consisting of n-octyl, n-nonyl, n-decyl, n-undecyl, n-dodecyl, n-tridecyl and n-tetradecyl.

33. A lubricating composition according to claim 15, the compound having 17 to 23 carbon atoms.

34. A lubricating composition according to claim 15, the compound having 24 to 30 carbon atoms.

35. A lubricating composition according to claim 15, the compound having 31 to 37 carbon atoms.

36. A lubricating composition according to claim 15, the compound having 38 to 44 carbon atoms.

37. A lubricating composition according to claim 15, the compound having 45 to 57 carbon atoms.

38. A lubricating composition according to claim 15 wherein the compound is selected from the group consisting of 8-methyl-8-heptyldecane
8-methyl-8-heptylhexadecane
9-methyl-9-heptylheptadecane
9-methyl-9-octylheptadecane
10-methyl-10-nonylnonadecane
10-methyl-10-octylnonadecane
9-methyl-9-octyloctadecane
11-methyl-11-decylhenicosane
11-methyl-11-nonylhenicosane
10-methyl-10-nonylicosane
12-methyl-12-decyltricosane
11-methyl-11-decyl docosane
12-methyl-12-undecyltricosane
8,8-diheptylpentadecane
8,8-diheptylhexadecane
9,9-diheptylheptadecane
9-heptyl-9-octylheptadecane
9,9-dioctylheptadecane
9,9-dioctyloctadecane
10,10-dioctylnonadecane
10-octyl-10-nonylnonadecane, and
10,10-dinonylnonadecane.

39. A lubricanting composition according to claim 38 wherein the compound is 9-methyl-9-octylheptadecane.

40. A lubricanting composition according to claim 38 wherein the compound is 11-methyl-11-decylhenicosane.

41. A lubricanting composition according to claim 38 wherein the compound is 9,9-dioctylheptadecane.

42. A lubricating composition according to claim 15 wherein the composition contains a mixture of at least two of the compounds and each of $R_1$, $R_2$, $R_3$ and $R_4$ is individually and independently selected from alkyl groups of varying carbon chain lengths.

43. A compound of the formula:

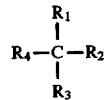

wherein $R_1$ is methyl or ethyl and $R_2$, $R_3$ and $R_4$ are the same or different and are straight chain alkyl groups having from 5 to 14 carbon atoms and wherein said compound has 38 to 44 carbon atoms.

* * * * *